United States Patent [19]
Mizuta

[11] Patent Number: 5,253,280
[45] Date of Patent: Oct. 12, 1993

[54] SAMPLE CELL SUPPORT ASSEMBLY FOR FLUORESCENT X-RAY ANALYSIS

[75] Inventor: Masao Mizuta, Kyoto, Japan
[73] Assignee: Horiba, Ltd., Kyoto, Japan
[21] Appl. No.: 877,969
[22] Filed: Apr. 30, 1992
[30] Foreign Application Priority Data
  May 3, 1991 [JP] Japan ................. 3-130635
[51] Int. Cl.⁵ ......................................... G01N 23/223
[52] U.S. Cl. ........................................ 378/45; 378/47; 378/208
[58] Field of Search ................... 378/47, 45, 208

[56] References Cited
U.S. PATENT DOCUMENTS
4,037,109 7/1977 Hosokawa et al. ............... 378/47
4,224,517 9/1980 Lubecki et al. ................. 378/47

Primary Examiner—Craig E. Church
Attorney, Agent, or Firm—Price, Gess & Ubell

[57] ABSTRACT

A fluorescent X-ray analyzer having a source of X-rays and a detector for measuring fluorescent X-rays utilizes a sample cell having an inner and outer cell frame that captures an X-ray transmissive member. The inner cell frame has a lower surface co-planar with a sample measuring surface defined by the X-ray transmissive member. A sample cell stand assembly includes an outer cell frame member and an inner cell frame member with respective apertures. An X-ray transmissive member extends across the central apertures. The inner stand frame member contacts the inner cell frame member to provide a fixed distance relationship between the detector and the sample measuring surface.

16 Claims, 5 Drawing Sheets

SAMPLE CELL SUPPORT ASSEMBLY FOR FLUORESCENT X-RAY ANALYSIS

BACKGROUND OF THE INVENTION

Field of the Invention

The present invention relates to a fluorescent X-ray analyzer, and more particularly to a unique support stand for accurately positioning a sample cell.

Description of Related Art

Fluorescent X-ray analysis provides an important investigatory tool for analyzing fluid samples, such as liquids and powders. Conventionally, fluorescent X-ray analyzers have placed the liquids or powders within a sample cell formed of a transmissive X-ray thin sheet, which in turn is positioned at a specific measuring position in the fluorescent X-ray analyzer. The sample cell is then subjected to primary X-rays from below the measuring position, and these primary X-rays will interact with the sample to generate a secondary emitted or fluorescent X-ray whose wavelength will be equaled to the emission line of that element. In contrast to absorption methods of analysis, a fluorescent X-ray technique gives essentially a surface analysis when used, for example, with a solid material. The accurate positioning of the sample cell is necessary to validate the measurement results.

Referring to FIG. 5, a conventional fluorescence X-ray analyzer is shown in a schematic form. A support bench 1 is provided with a turntable 4 for supporting a sample cell 3. The measuring position 2 is positioned at set or fixed distance from the X-ray detector 6 so that it is capable of detecting fluorescence X-rays generated by the application of the primary X-rays from the X-ray tube 5. These X-rays from the X-ray tube 5 will be applied directly to the sample cell 3. An incident surface 7 is provided on the detector 6 for receiving the fluorescent X-rays. As can be appreciated, the sample cell 3 should be transmissive of the primary X-rays and further capable of housing, for example, a fluid sample. A construction of such a sample cell can be further seen in FIG. 5 and includes a cylindrical cell inner frame 8 formed of a plastic, such as polyethylene, or even of a metal. Referring to FIG. 4, one form of a sample cell is disclosed wherein the cylindrical cell inner frame is shown in a perspective view having a series of circular projections 9, 10, 11 on its outer surface. An inner frame cover 12 can be formed by bending a soft plastic film to form a circular bottom 13, a circular riser member 14 rising so as to surround the bottom 13 and a folder member 15 extending from an upper end of the riser member 14. A flange member 16 is connected with the folded member 15 and a spacer gap 17 is provide to receive the cell inner frame 8. Thus, the cell inner frame 8 is positioned between the riser member 14 and the folded member 15. A reinforcing paste board 18 can be adhered to a backside of a bottom 13 and also to a backside of the flange member 16.

An X-ray transmissive sheet 19 made, for example, of Mylar (trade name) and the like can be utilized to enclose the sample cell opening which is bounded by the walls of the riser member 14. A cylindrical cell outer frame 20 can be made of plastic, such as polyethylene or instead can be made of a metal. The outer frame member 20 has an exterior flange member 21 integrally formed at one end and an interior projection 22.

Thus, the mounting structure for the sample cell 3 includes a turntable 4, an outer cylindrical cell frame 20, a plastic film frame cover 12, an X-ray transmissive sheet 19, and a cell inner frame 8.

In order to charge or fill the sample cell 3 with an appropriate sample, the cell inner frame 8 is inserted into the space 17 of the inner frame cover 12 to thereby cover the cell inner frame 8 with the riser member 14 and the folded member 15 of the inner frame cover 12. This structure provides a cavity configuration that can receive the sample as it is put into the space formed by the bottom 13 and the riser member 14 of the inner frame cover 12. The sample is then covered with the X-ray transmissive sheet 19 which is mounted above the inner frame cover 12. Subsequently, the outer cell frame 20 is mounted across the X-ray transmissive sheet 19 to capture it and thereby close the cavity inside of the cell inner frame 8, while keeping a relatively smooth and taut position.

When used for an analysis procedure, the sample cell 3, as configured above, is placed on the measuring position 2 in an inverted arrangement, as shown in FIG. 5. The sample 23, as captured within the sample cell 3, is then subject to primary X-rays from the X-ray tube 4, which penetrates through the X-ray transmissive sheet 19 of the sample cell 3. These primary X-rays then induce the secondary fluorescence X-rays to be exited by the elements to be analyzed within the sample 23 and these X-rays are then detected by means of the X-ray detector 6 thereby enabling an energy measurement of the intensity of the fluorescence X-rays.

As can be further seen in FIG. 5, in this particular arrangement of the sample cell 3, the X-ray transmissive sheet 19 is positioned slightly above a lower end portion of the cell outer frame 20 when the sample cell 3 is mounted on the turntable 4. The cell outer frame 20 of the sample cell 3 is directly placed on the upper surface of the turntable 4 and this arrangement creates a distance (a) between a measuring surface (A) of the sample (an outer surface of the X-ray transmissive sheet 19) and the X-ray detector 6. In such an arrangement this distance (a) between the measuring surface (A) of the sample cell and the X-ray detector 6 is defined by the relationship of placing the cell outer frame 20 of the sample cell directly on the upper surface of the turntable 4, and problems can occur in that the measuring surface (a) of the sample cell can be shifted in position during the assembly of the outer cell and during its alignment on the turntable 4. As a result, the measuring surface (a) of the sample cell can fluctuate within a distance (b) between the cell outer frame 20 and the measuring surface (a) of the sample, which can contribute to a variance in the distance between the measuring surface (A) of the sample and the X-ray detector 6. As a result of any fluctuation of the total distance (a), the fluorescence X-rays generated when the sample cell 3 is irradiated with the primary X-rays have a property of being absorbed by air to reduce an intensity thereof. Thus, any fluctuation in the distance (a) would increase the quantity or contact of the fluorescence X-rays with the air and thereby can provide analytical errors in the resulting measurement.

These problems can occur not only in the case where the sample cell of the construction shown in FIG. 4 is used, but also in those cases where a sample cell comprising a cell outer frame 20, a cell inner frame 8 provided inside the cell outer frame 20, and an X-ray transmissive sheet 19 placed between the cell outer frame 20 and the cell inner frame 8 to closed one end side of the cell inner frame 8 is set at a measuring position 2, as shown, for example, in FIG. 5. Thus, the prior art is still seeking to optimize the construction and mounting of sample cells to eliminate errors.

SUMMARY OF THE INVENTION

It is an object of the present invention to provide a fluorescent X-ray analyzer capable of accommodating a sample cell so that a distance between a measuring surface of a sample, contained within the sample cell, and an X-ray detector will be maintained always at a constant distance, regardless of the number of times the sample cell is aligned on the analyzer, thereby assuring a highly accurate analysis.

To accomplish these purposes, a sample cell stand is provided with a circular projection that can be brought into direct contact with a bottom surface of a sample cell to thereby ensure that the sample cell measuring position will be accurately maintained. A guide portion, guiding the sample cell, can include a stand outer frame that is readily positioned outside of the sample cell and may be detachably arranged at the measuring position. The sample cell stand may comprise a stand outer frame and a stand inner frame with an X-ray transmissive sheet placed between the stand outer frame and the stand inner frame to close one end side of the stand inner frame.

As a result of such a construction, a sample cell can be mounted in a fluorescence X-ray analyzer so that the bottom surface of the sample cell is placed directly on a circular projection of the sample cell stand so that the distance between the measuring surface of the sample and the X-ray detector will remain constant to achieve a highly accurate analysis.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide sample cell support structure.

Figure 1:
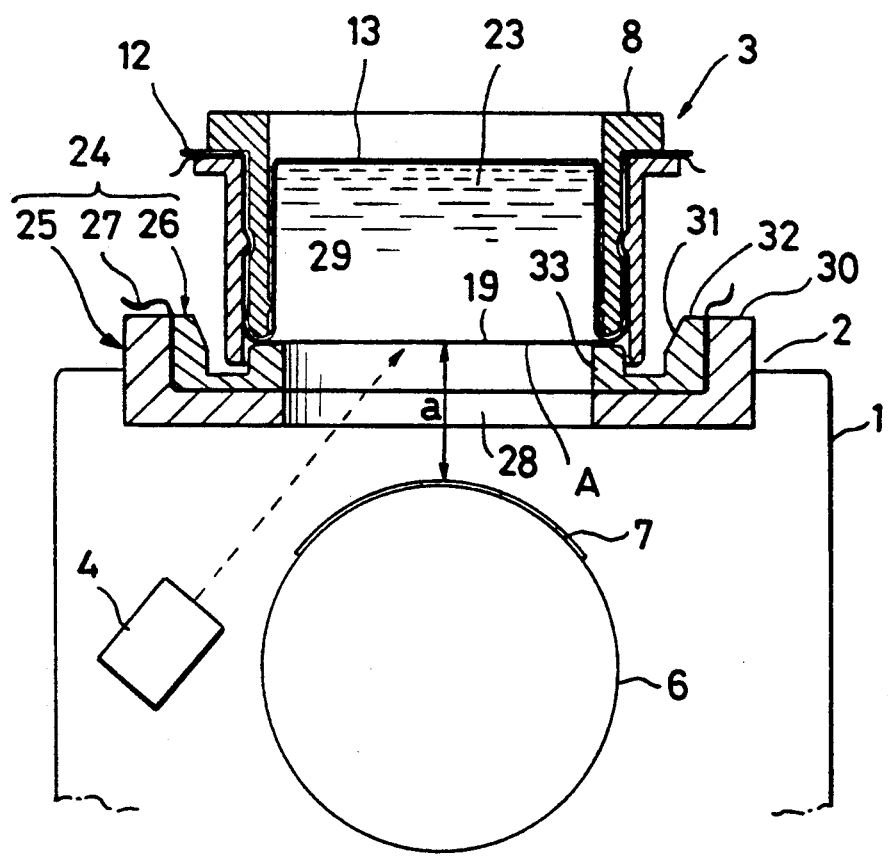
FIG. 1 is schematic cross-sectional configuration showing the relevant portions of a fluorescence X-ray analyzer and a sample cell support structure according to a first embodiment of the present invention.
Figure 4:
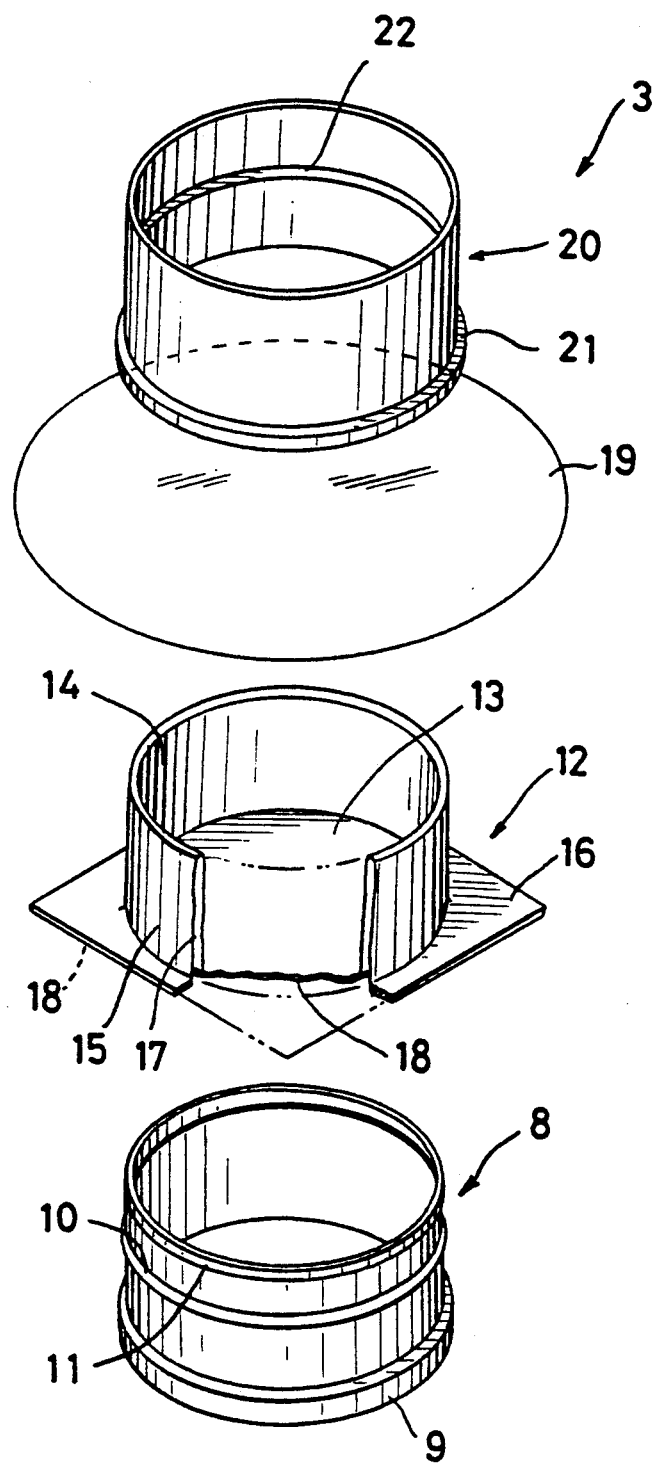
FIG. 4 is an exploded perspective view showing the construction of a sample cell.
Figure 5:
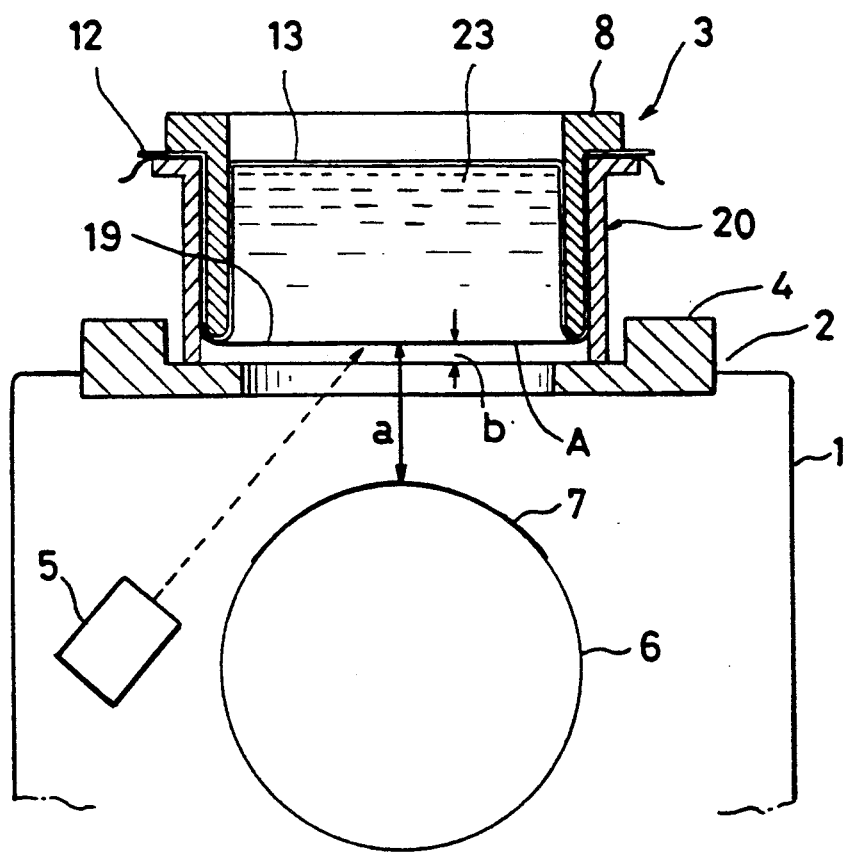
FIG. 5 is a schematic cross-sectional view of a conventional support structure for a sample cell on a fluorescence X-ray analyzer.

Referring to FIG. 1, a cross-sectional view of one embodiment of the present invention is disclosed as mounted in a fluorescence X-ray analyzer system. For ease of convenience, the same reference numbers for the same elements disclosed in FIGS. 4 and 5 will be utilized in the description of FIG. 1. Thus, the sample cell for holding a sample 23 can include the same type of cylindrical cell inner frame 8 with the same soft plastic film bent to form a circular bottom 13 and mounted to be captured by an outer cylindrical frame 20. An X-ray transmissive sheet 19 is also captured between the cell inner frame 8 and the cell outer frame 20. The sample cell 3 can be mounted on a sample cell stand assembly 24 that is detachably arranged at a measuring position 2 on the bench 1. One example of such a sample cell stand assembly 24 is disclosed in FIG. 2.

The sample cell stand assembly 24 comprises a stand outer frame 25, a stand inner frame 26 that can be mounted or nestled inside the stand outer frame 25, and an X-ray transmissive sheet 27 that can be captured between the stand outer frame 25 and the stand inner frame 26 to close one side of the stand inner frame 26. The inner and outer stand frames 25 and 26 can be formed of a circular configuration having a central aperture or space portion 28 and 29, respectively. Each of these members can have the same diameter aperture and can be made of aluminum.

Figure 2:
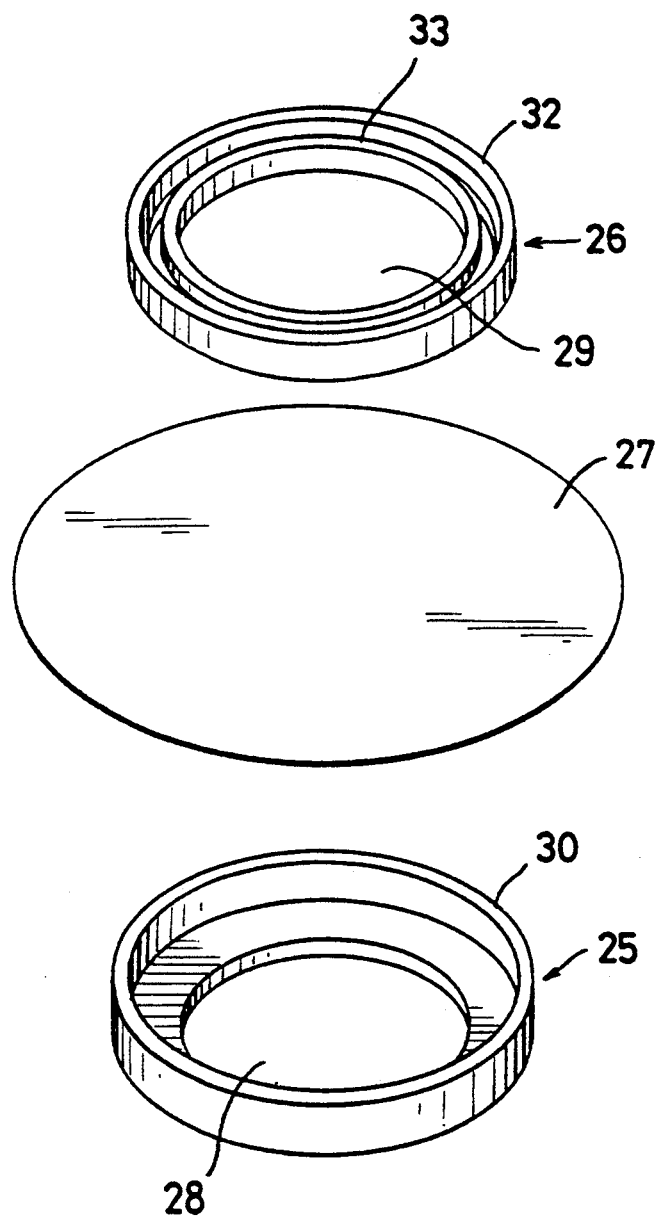
FIG. 2 is an exploded perspective view showing one example of a sample cell stand structure for use in the fluorescence X-ray analyzer.

The stand outer frame 25 is further provided with a circular riser member 30 having a suitable height along an outer edge portion thereof. The stand inner frame 26 has a diameter slightly smaller than that of the stand outer frame 25 and is also provided with a circular guide member 32 that can be closely dimensioned to an inner surface of the riser member 30 so that it just accommodates the thickness of the X-ray transmissive sheet 27 when it is positioned between the stand outer frame 25 and the stand inner frame 26, as shown in FIG. 2. The stand inner frame 26 has a tapered inner circumferential surface 31 that is sloped outward so as to guide a sample cell 3, if necessary, during its insertion into the stand assembly 24. An inner circular projection 33 is formed concentrically with the guide member 32 with an annular recess extending between the two members. With regard to the specifics of the dimensions of the stand outer frame 25 and the stand inner frame 26, it is sufficient that, as shown in FIG. 1, the dimensions enable the sample cell 3 to be set so that a bottom surface of the sample cell 3, in particular the lower end of the cell inner frame 8, can directly contact a flat upper end of the circular projection 33, while the sample cell outer frame 20 is positioned between the riser member 31 and the circular projection 33. Thus, an outside diameter of the circular projection 33 is slightly less than an inside diameter of the cell outer frame 20 and, preferably, of a dimension so that the lower end of the cell inner frame 8 will not be offset from the upper end of the circular projection 33, even if the sample cell 3 is shifted in a horizontal direction. Thus, the lower end of the inner cell frame 8 will rest, as shown in FIG. 1, on the upper edge of the circular projection 33. Preferably, the guide member 32 is to be higher than the circular projection 33 with the recess between the respective projection members being sufficient to not contact the lower end of the cell outer frame 20.

The X-ray transmissive sheet 27 can be made out of the same type of material as that of the X-ray transmissive sheet 19, e.g., Mylar. The X-ray transmissive sheet 27 is also stretched or extended by the stand inner frame 26 so that it is not crumpled or formed with any crease between the stand inner frame 26 and the stand outer frame 25. The X-ray transmissive sheet 27 partitions the space portions 28 and 29 between the bottom surface of the sample cell 3 and the fluorescence X-ray detector 6.

In operation, the sample cell stand assembly 24 is assembled, as described above, and is placed at the measuring position 2 on the bench 1. The sample cell 3, which has been separately assembled so as to house a sample 23 therein, is then set at the measuring position 2 so that the lower end of the cell inner frame 8 may correspond to the upper end of the circular projection 33. In this position, the sample 23 within the sample cell 3 can be subjected to primary X-rays from an X-ray tube 4 through the X-ray transmissive sheet 27 of the sample cell stand 24 and also through the X-ray transmissive sheet 19 of the sample cell 3. Interaction of these primary X-rays with the sample elements will produce a fluorescent X-ray that is exited by the elements to be analyzed, contained in the sample cell 23, and these fluorescent X-rays can be detected by the X-ray detector 6 to measure the energy intensity of these fluorescent X-rays.

As can be appreciated, the guide member 32 on the inner frame 26 could contact the cell outer frame 20 projecting below the cell inner frame 3 when the operator is attempting to set the sample cell in place. The incline surface 31 can help in centering the sample cell to enable an easy positioning of the lower end of the inner cell frame 8 onto the circular projection 33, thereby preventing not only an inadvertent breakage of the sample cell 3 due to an engagement with the projecting portions of the X-ray transmissive sheet 19 but also facilitating a quick and easy assembling of the sample cell 3 in the measuring position. In this position, the distance (a) between a measuring surface (A) of the sample and the X-ray detector 6 will always remain constant and thus the quantity or degree of contact of the fluorescent X-rays with air will not fluctuate between the positioning of various sample cells 3 on the stand assembly 24. The inclusion of the X-ray transmissive sheet 27 serves an additional function in that it isolates the sample cell and the sample 23 within the sample cell 3 from the X-ray detector 6 so that, if there is any rupture or leaking of the sample cell 3, the sample cell stand 24 will receive the sample 23 to prevent any leaked-out sample from doing any harm or contamination to the X-ray detector 6, the X-ray tube 4 and the corresponding equipment (not shown).

As can be readily appreciated, the sample cell stand assembly 24 is not only easily detachable relative to the measuring position 2 of the bench 1, but can also be easily assembled and disassembled so that any maintenance or replacement of parts can be easily accomplished by the operator. Additionally, cleaning of the X-ray transmissive sheet 27, the stand inner frame 25 and the stand outer frame 26 can be accomplished.

Figure 3:
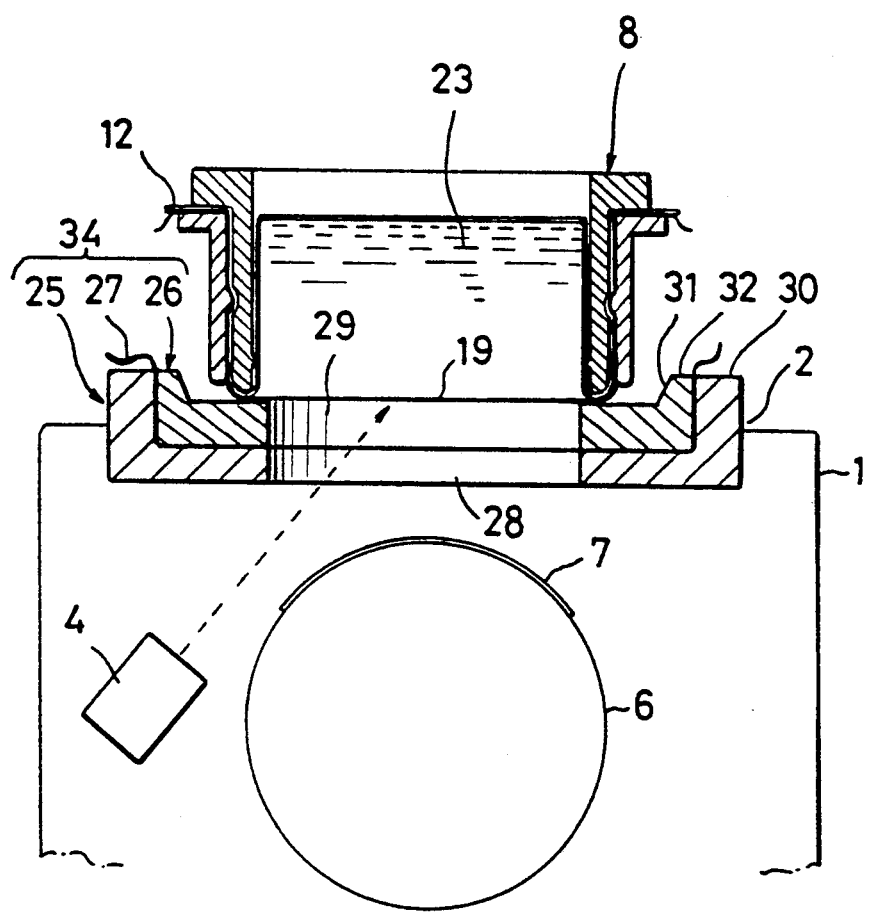
FIG. 3 is a schematic cross-sectional view showing a second embodiment of the present invention.

FIG. 3 discloses another embodiment of the present invention that is particular advantageous with an modified sample cell configuration. In this regard, the sample cell assembly 34 is provided with a modified stand inner frame 26', but does not have any recessed or inner circular projection. This is particular advantageous when the sample cell has a modified or shortened outer cylindrical cell frame 20'. Thus, the cell inner frame 8 is projected below the cell outer frame 20' so that it contacts its lower peripheral edge directly against the lower surface of the stand inner frame 26.

An alternative embodiment, not disclosed, is also possible where the cell inner frame 8 and the cell outer frame could be carefully dimensioned to both simultaneously engage with the support surface of the stand inner frame 26 of the sample cell stand 34.

Various modifications can be accomplished within the designed purposes of the present invention, for example, it is sufficient if the sample cell 3 comprises the cell outer frame 20, the cell inner frame 8, and an X-ray transmissive sheet 19, which is positioned between the cell outer frame 20 and the cell inner frame 8 to close one end side of the cell inner frame 8. The sample cell stands 24 and 34 could be incorporated directly into the turntable and the like. In addition, in a preferred embodiment, shown in FIG. 1, the cell inner frame 8 is adapted to project below the cell outer frame 20, however, the lower ends of both the cell outer frame 20 and the cell inner frame 8 may be adapted to be simultaneously engaged with the circular projection 33 of the stand inner frame 26.

As a result of the present invention, a sample cell can be held so that the distance between the measuring surface of the sample and the X-ray detector may be always constant, regardless of the number of times that the sample cell is assembled onto the supporting stand assembly.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a fluorescent X-ray analyzer having means for providing X-rays and means for detecting fluorescent X-rays emitted from an irradiated sample, the improvement comprising:

a sample cell having an inner and outer cell frame with central apertures and a first X-ray transmissive member extending between the inner and outer cell frames and across the apertures to define a sample measuring surface, the inner cell frame having a lower surface co-planar with the sample measuring surface, and a sample cell stand assembly including an outer stand frame member and an inner stand frame member with respective central apertures and a second X-ray transmissive member extending across the central apertures, the sample cell stand assembly mounting the sample cell to receive X-rays and to provide a determined fixed distance relationship between the detecting means and the sample measuring surface.

2. The invention of claim 1 wherein the sample cell inner frame is nestled within the outer cell frame and extends below the outer cell frame to contact the inner stand frame member for support.

3. The invention of claim 1 wherein the sample cell inner frame is nestled within the outer cell frame and the outer cell frame extends below the inner cell frame, the inner cell frame contacts the inner stand frame member for support.

4. The invention of claim 1 wherein the inner stand frame member includes a circular projection dimensioned to correspond to at least a dimension of the sample cell inner frame for direct contact.

5. The invention of claim 4 wherein the inner stand frame member includes an annular groove and the stand outer frame member includes a peripheral rim member.

6. The invention of claim 5 further including means to align the sample cell in the inner frame member including a sloping annular surface.

7. A support frame assembly for positioning a sample cell in a fluorescent X-ray analyzer comprising:
   a stand outer frame;
   a stand inner frame detachable positioned inside the stand outer frame, and
   an X-ray transmissive sheet positioned between the stand outer frame and the stand inner frame to close one side of the stand inner frame.

8. A support frame assembly as set forth in claim 7 wherein the stand outer frame includes a peripheral rim member and the stand inner frame includes an annular groove.

9. A support frame assembly as set forth in claim 8 wherein the X-ray transmissive sheet is captured in a smooth planar configuration across a central portion between the peripheral rim member and the stand inner frame.

10. A support frame assembly as set forth in claim 9 wherein the inner frame includes a central aperture with a raised circular projection around the central aperture.

11. In a fluorescent X-ray analyzer having a sample cell including a cell outer frame, a cell inner frame positioned within the cell outer frame and an X-ray transmissive sheet positioned between the cell outer frame and the cell inner frame to close one end of the sample cell and to define a measuring interface surface, the improvement comprising:
   a sample cell stand assembly including an inner stand frame member having a support surface to directly contact a sample cell frame coincidental with the measuring interface surface to provide an easily definable measurement distance to the sample cell, and an outer stand frame member, the inner stand frame member includes a circular projection dimensioned to correspond to at least a dimension of the sample cell inner frame for direct contact, the sample cell stand assembly further includes an X-ray transmissive sheet positioned between the inner and outer stand frame members.

12. A fluorescent X-ray analyzer of claim 11 further including means to align the sample cell in the inner stand frame member including a sloping annular surface.

13. A fluorescent Xray analyzer of claim 12 wherein the inner and outer stand frame members have a central aperture.

14. In a fluorescent X-ray analyzer having a sample cell including a cell outer frame, a cell inner frame positioned within the cell outer frame and an X-ray transmissive sheet positioned between the cell outer frame and the cell inner frame to close one end of the sample cell and to define a measuring interface surface, the improvement comprising:
   a sample cell stand assembly including an inner stand frame member having a support surface to directly contact a sample cell frame coincidental with the measuring interface surface to provide an easily definable measurement distance to the sample cell, and an outer stand frame member, the inner stand frame member includes a circular projection dimensioned to correspond to at least a dimension of the sample cell inner frame for direct contact, the inner stand frame member includes an annular groove and the stand outer frame member includes a peripheral rim member for interfacing with the annular groove, the sample cell stand assembly further includes an X-ray transmissive sheet positioned between the inner and outer stand frame members.

15. A fluorescent X-ray analyzer of claim 14 further including means to align the sample cell in the inner stand frame member including a sloping annular surface.

16. A fluorescent X-ray analyzer of claim 14 wherein the inner and outer stand frame members have a central aperture.

* * * * *